United States Patent
Ruth et al.

(10) Patent No.: US 6,210,640 B1
(45) Date of Patent: Apr. 3, 2001

(54) COLLECTOR FOR AN AUTOMATED ON-LINE BATH ANALYSIS SYSTEM

(75) Inventors: Kenneth A. Ruth, Warrenton; Philip R. Schmidt, St. Charles, both of MO (US)

(73) Assignee: MEMC Electronic Materials, Inc., St. Peters, MO (US)

( * ) Notice: Subject to any disclaimer, the term of this patent is extended or adjusted under 35 U.S.C. 154(b) by 0 days.

(21) Appl. No.: 09/093,520

(22) Filed: Jun. 8, 1998

(51) Int. Cl.[7] ................................................ G01N 1/20
(52) U.S. Cl. ................ 422/81; 422/68.1; 422/100; 436/343; 436/52; 73/864.85; 73/863.52
(58) Field of Search ................ 422/63, 68.1, 81, 422/100, 102, 103, 104; 436/43, 52, 54, 174, 180; 73/864.21, 863.52, 864.83, 864.84, 864.85

(56) References Cited

U.S. PATENT DOCUMENTS

| | | | |
|---|---|---|---|
| 3,583,235 | 6/1971 | Tanila | 73/423 |
| 3,691,391 | 9/1972 | Kishi | 250/218 |
| 3,849,002 | 11/1974 | Hach | 356/103 |
| 4,515,753 | * 5/1985 | Smith et al. | 422/102 |
| 4,638,675 | * 1/1987 | Sperinck et al. | 73/864.34 |
| 4,774,057 | * 9/1988 | Uffenheimer et al. | 422/100 |
| 4,873,057 | * 10/1989 | Robertson et al. | 422/75 |
| 4,910,151 | * 3/1990 | Platt | 436/163 |
| 4,990,459 | 2/1991 | Maeda et al. | 436/178 |
| 4,999,305 | * 3/1991 | Wolcott et al. | 436/52 |
| 5,156,813 | * 10/1992 | Calhoun | 422/102 |
| 5,633,172 | 5/1997 | Shimazaki | 436/177 |
| 5,647,386 | 7/1997 | Kaiser | 134/113 |
| 5,723,093 | 3/1998 | DeBruyne et al. | 422/81 |
| 5,741,709 | * 4/1998 | Hsu | 436/52 |
| 5,837,203 | * 11/1998 | Godec et al. | 422/100 |

FOREIGN PATENT DOCUMENTS 0 474 607 A2    3/1992    (EP) .

OTHER PUBLICATIONS

PCT International Search Report for PCT/US99/12735, dated Sep. 24, 1999.

* cited by examiner

Primary Examiner—Lyle A. Alexander
(74) Attorney, Agent, or Firm—Senniger, Powers, Leavitt & Roedel

(57) ABSTRACT

A collector and method for collecting samples of liquid from at least one source of liquid for automated analysis of the samples. The collector has at least one receptacle for receiving liquid from the source of liquid and holding a quantity of the liquid for obtaining a sample. Each receptacle has an inlet for delivery of liquid from the respective source of liquid and an open top sized to admit the sample collection device into the receptacle. The collector also has a spillway in fluid communication with the open top of the receptacle for receiving excess liquid spilling over the open top of the receptacle. The collector is constructed so that liquid continuously flows through the collector. A drain of the collector receives liquid from the spillway for draining the liquid from the collector.

9 Claims, 3 Drawing Sheets

COLLECTOR FOR AN AUTOMATED ON-LINE BATH ANALYSIS SYSTEM

BACKGROUND OF THE INVENTION

The present invention generally relates to a collector for collecting liquid samples from a source of liquid. More particularly, the present invention relates to a collector for collecting samples of liquid from at least one semiconductor wafer cleaning bath so that automated analytical instrumentation can analyze the samples for contamination.

Semiconductor wafers suitable for the fabrication of integrated circuits are produced by slicing thin wafers from a single crystal silicon ingot. After slicing, the wafers undergo a lapping process to give them a substantially uniform thickness. The wafers are then etched to remove damage and produce a smooth surface. The next step in a conventional wafer shaping process is a polishing step to produce a highly reflective and damage-free surface on at least one face of the wafer. It is upon this polished face that electrical device fabrication takes place.

The presence of contaminants on the surface of a semiconductor wafer can greatly diminish the quality and performance of integrated circuits fabricated from the wafer. Thus, semiconductor wafers are typically cleaned after some or all of the above wafer preparation steps to help reduce the amount of contamination present on the final wafer product. For example, organic and other particulate contaminants can be removed from the surfaces of a single crystal silicon wafer by immersing the wafer in each of a series of cleaning bath solutions.

Monitoring the concentration of contaminants in a semiconductor cleaning bath solution serves several useful purposes. First, the useful life of the cleaning bath solution can be maximized. As wafers are continuously processed through a particular cleaning bath, the concentration of contamination in the cleaning bath solution will generally rise. Ultimately, the cleaning bath solution becomes saturated with contamination, and will no longer adequately clean the wafer. By monitoring the concentration of contaminants present in a particular cleaning bath solution, the point at which the solution is spent can be more accurately determined.

The second advantage realized by monitoring the concentration of contaminants in a cleaning bath solution is that sources of contamination can be more accurately identified. The various reagents used to make up the cleaning bath solution may contain impurities that actually contaminate the wafer, as opposed to cleaning it. The preparation of purer cleaning bath solutions requires the identification and elimination of these sources of contamination, which are more easily accomplished by monitoring the concentration of contaminants in a cleaning bath.

The accuracy and reliability of the analytical data obtained by the monitoring of cleaning baths greatly impact both the identification of the source of a contaminant and the determination of the useful life of a cleaning bath. In addition, because even low levels of some impurities can result in wafer surface contamination, the sensitivity of the analytical method is also critical.

Traditionally, the type and concentration of a contaminant in a cleaning bath solution have been monitored through the use of a manual sampling technique, commonly referred to as an "off-line" method of sampling, wherein a human operator collects a sample of the cleaning bath solution. The sample is then transported to a laboratory for analysis.

One disadvantage of this off-line sampling method is that it is prone to the introduction of additional contaminants from outside sources. For example, human contact with the sample can lead to the introduction of contaminants such as aluminum, iron, calcium, and sodium. In addition, the vial or container which holds the sample, as well as the pipette or other sampling device, typically cannot be sufficiently cleaned to avoid the introduction of outside contaminants into the sample. Thus, this off-line sampling method lacks the accuracy and sensitivity needed to provide representative results of the actual condition of the cleaning bath solution being tested.

Also, it can take up to several hours for a laboratory to complete the analysis of the sample and provide the results to the operators responsible for wafer cleaning. In the interim period, if wafer cleaning continues, a bath containing highly contaminated solution can produce hundreds of unacceptable wafers. This necessitates the recall and re-cleaning of these wafers. Alternatively, use of the bath could be halted while operators wait for the results. In either case, the net effect is an increase in production cost and a decrease in overall efficiency of the cleaning process.

To avoid the time consuming and potentially costly process of laboratory analysis, it has become common practice to simply discard the cleaning solution after a predetermined period of time, such as every 12 hours. However, the many variables which dictate the useful life of a cleaning bath solution, including the quality of the chemical reagents, the quality of the process water, the cleanliness of the wafers immersed in the solution, and the precautions taken to prevent contamination by human operators, are not taken into account under such a method. Therefore, without the benefit of an analysis for contaminants, a portion of the useful life of the bath may be wasted.

To overcome the above disadvantages, the concentration of impurities in a cleaning bath solution can be determined by an "on-line" process which allows for the sampling and analysis of the cleaning solution in a single, integrated process. That is, a sample is mechanically removed from a cleaning bath solution and automatically analyzed by analytical instrumentation without being directly exposed to an environment in which a human operator is present. An example of such a process is the co-assigned U.S. application, incorporated herein by reference, filed the same date as the present application, naming Larry W. Shive and Erik J. Mori as inventors, and entitled "Process for Monitoring the Concentration of Metallic Impurities in a Wafer Cleaning Solution."

A mechanical sampling and automated analysis system should preferably be constructed to ensure that the sample obtained from the cleaning bath is representative of the cleaning bath as a whole. If the sample obtained is not representative of the cleaning bath, accurate and reliable contamination measurements may not be obtained. To help ensure that the sample obtained is representative of the cleaning bath as a whole, the on-line system must not be a source of contamination itself. For instance, if valves were used in the on-line system to intermittently collect a sample, they may ultimately wear and introduce contamination into the sample that is not present in the cleaning bath as a whole, causing inaccurate contamination measurements.

Further, when multiple baths are to be sampled, it may be impractical to mechanically remove a sample from the cleaning baths themselves because the baths are typically positioned a significant distance away from each other. In this instance, a collection device may be needed to facilitate automated analysis. The collection device can maintain a portion of the cleaning bath solution from each bath in separate receptacles, all the receptacles being in close proximity to each other. If the collected portion of the cleaning solution is allowed to stagnate, however, the sample removed therefrom will not be representative of the cleaning bath as a whole and inaccurate contamination measurements will result.

SUMMARY OF THE INVENTION

Among the objects of the present invention, therefore, are the provision of a collector for collecting samples of liquid from a cleaning bath which allows for sample collection and analysis of the contaminants in the solution via an on-line process; the provision of such a collector which allows for analysis of the contaminants in a cleaning bath solution via an on-line process without delaying the wafer cleaning process; the provision of a collector which allows for reliable and reproducible analysis of the contaminants in a wafer cleaning bath solution via an on-line process; and the provision of such a collector which reduces the risk of contamination of the cleaning bath solution.

Briefly, therefore, the present invention is directed to a collector for collecting samples of liquid from at least one source of liquid for automated analysis of the samples, comprising at least one receptacle, adapted for receiving liquid from said at least one source of liquid and holding a quantity of the liquid for obtaining a sample. Each receptacle having an inlet for delivery of liquid thereinto from the respective source of liquid and an open top sized to admit the sample collection device into the receptacle. The collector also comprises a spillway in fluid communication with the open top of the receptacle for receiving excess liquid spilling over the open top of the receptacle. The collector further comprises a drain located for receiving liquid from the spillway for drainage of the liquid from the collector.

The present invention is further directed to a sample collection and analysis system for use in monitoring content of a liquid, generally comprising a bleed line adapted for continuously open fluid communication with at least one source of liquid. A collector in continuously open fluid communication with the bleed line, includes a receptacle to receive liquid from said at least one source of liquid and to hold a quantity of the liquid for obtaining a sample. The receptacle has an inlet for receiving liquid into the receptacle from the bleed line and an open top. The bleed line and the collector are free of structure capable of obstructing the flow of liquid from the source of liquid to the collector receptacles. The collection and analysis system further comprises a sample collecting device for collecting a sample of the liquid from the receptacle and a liquid analysis device for receiving liquid from the sample collecting device and automatically analyzing the liquid for its content.

The present invention is still further directed to a process for collecting and analyzing the content of a liquid from at least one source of liquid, the process comprising bleeding the liquid continuously from the source of liquid through a bleed line to a receptacle of a collector. The receptacle has an inlet at its bottom for receiving liquid into the receptacle and an open top. Next, the liquid is continuously delivered into the receptacle from the inlet to the open top of the receptacle, so that the liquid continuously flows from the bottom of the receptacle to the open top and continuously spills over the open top of the receptacle into a spillway of the collector. A sample of the liquid is drawn from the receptacle by an automated sample collecting device and then deposited from the sample collecting device into a liquid analysis device. Finally, the liquid is analyzed to determine its content.

Other objects and features of this invention will be in part apparent and in part pointed out hereinafter.

BRIEF DESCRIPTION OF THE DRAWINGS

Corresponding reference characters indicate corresponding parts throughout the drawings.

DETAILED DESCRIPTION OF THE PREFERRED EMBODIMENTS

Figure 1:
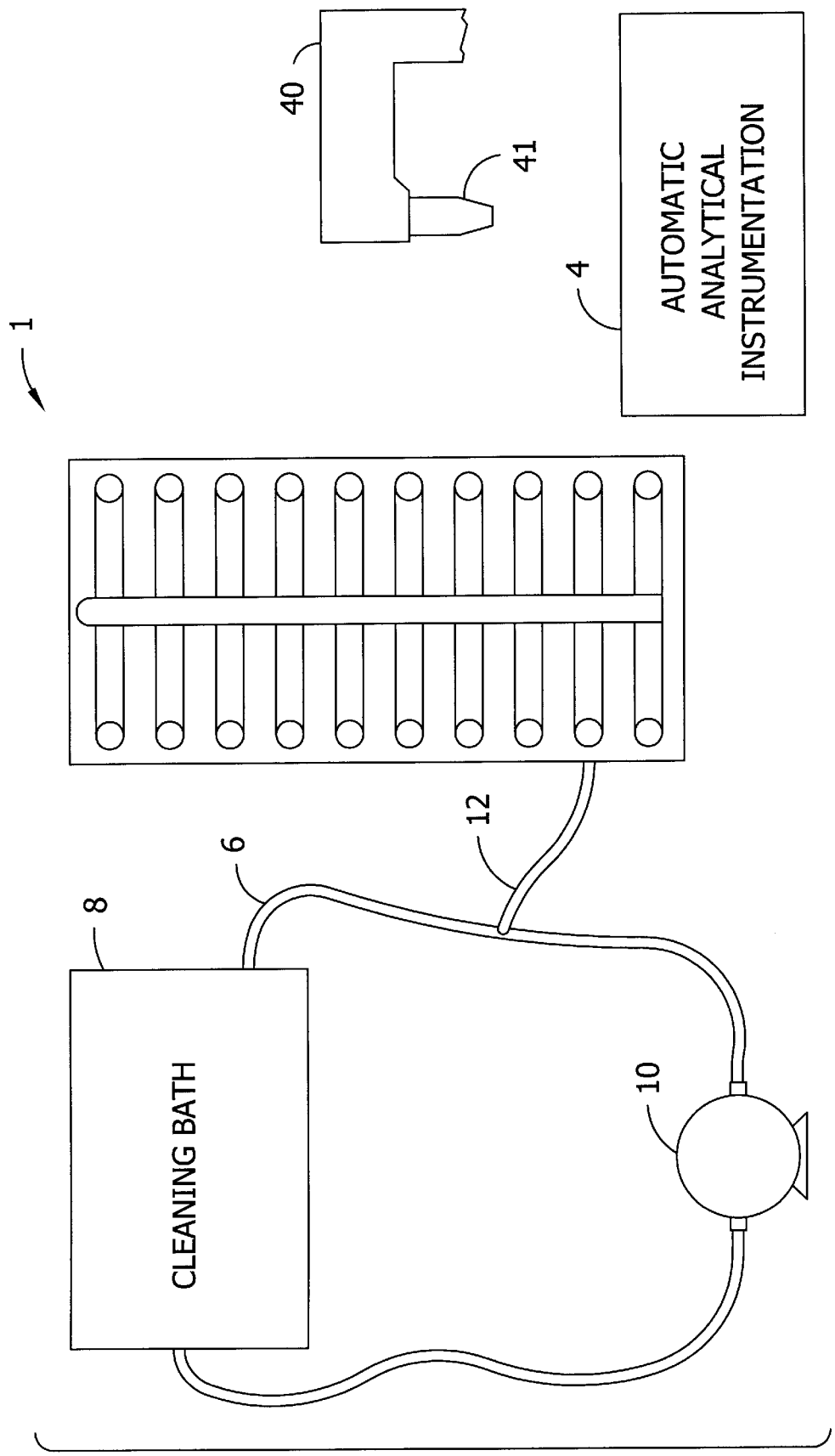
FIG. 1 is a schematic view of an on-line wafer cleaning system incorporating a collector of the present invention.

With reference to FIG. 1, a collector of the present invention for use in collecting samples of liquid from a cleaning bath is generally indicated at 1. The collector is preferably part of an "on-line" device (including the collector 1 and automatic analytical instrumentation 4) for sampling and analyzing a liquid, such as a cleaning bath solution, contained in a cleaning bath 8 for cleaning semiconductor wafers. The construction and operation of such on-line sampling and analysis device, with the exception of the collector described herein, is well known to those of ordinary skill in the art, and will not be further described in detail herein.

The collector 1 is connected to a recirculation line 6 of the cleaning bath 8 by a suitable bleed line 12. As recirculation pump 10 continuously circulates cleaning solution through the cleaning bath, a small portion of the cleaning solution in the cleaning bath is bled off into the bleed line 12 for delivery to the collector 1. Since the solution diverted through the feed line is typically not returned to the cleaning bath 8, the diameter of the feed line is preferably minimized to prevent excessive depletion of the cleaning solution from the bath. For example, the bleed line 12 of the illustrated embodiment is less than about ¼" in diameter, more preferably about ⅛" in diameter, and most preferably about ¹⁄₁₆" in diameter. The automated analytical instrumentation 4 is positioned in close proximity to the collector 1 to facilitate access by the analytical instrumentation to the samples collected by the collector.

Figure 2:
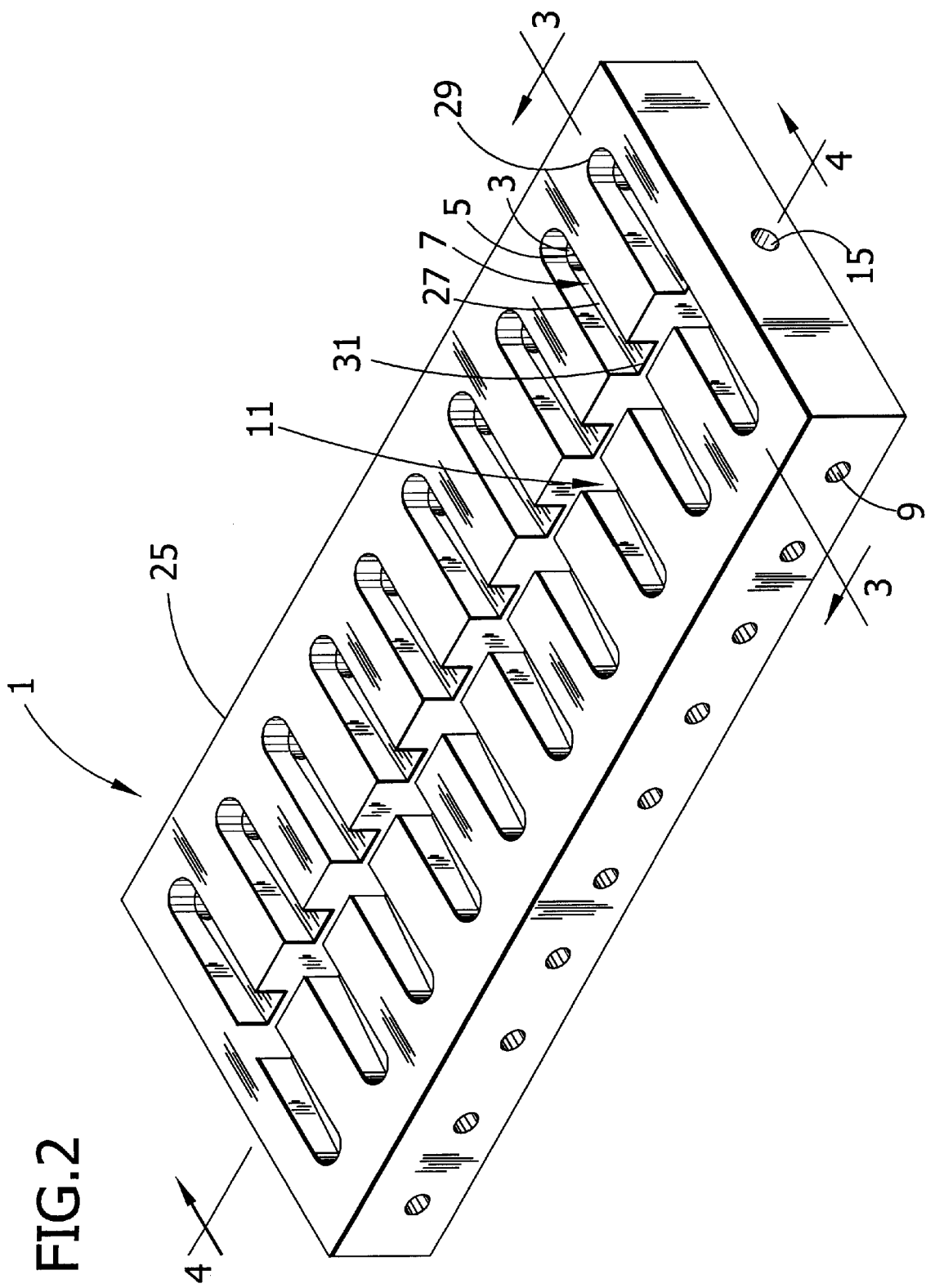
FIG. 2 is a perspective view of the collector of FIG. 1.
Figure 3:
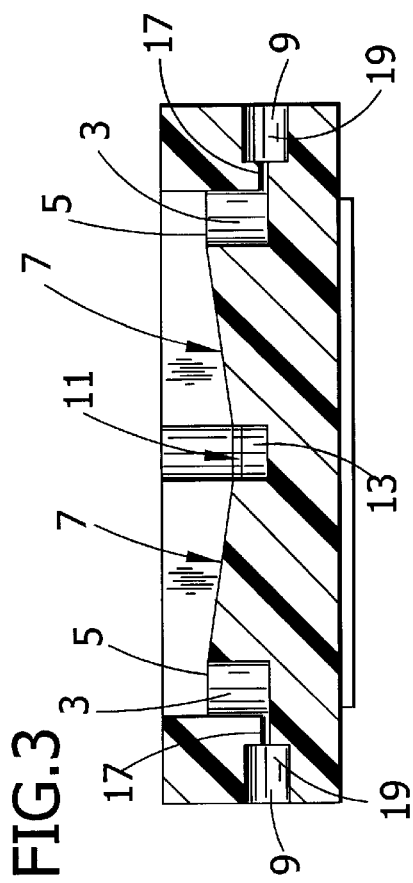
FIG. 3 is a sectional view taken along the plane of line 3—3 of FIG. 2.
Figure 4:
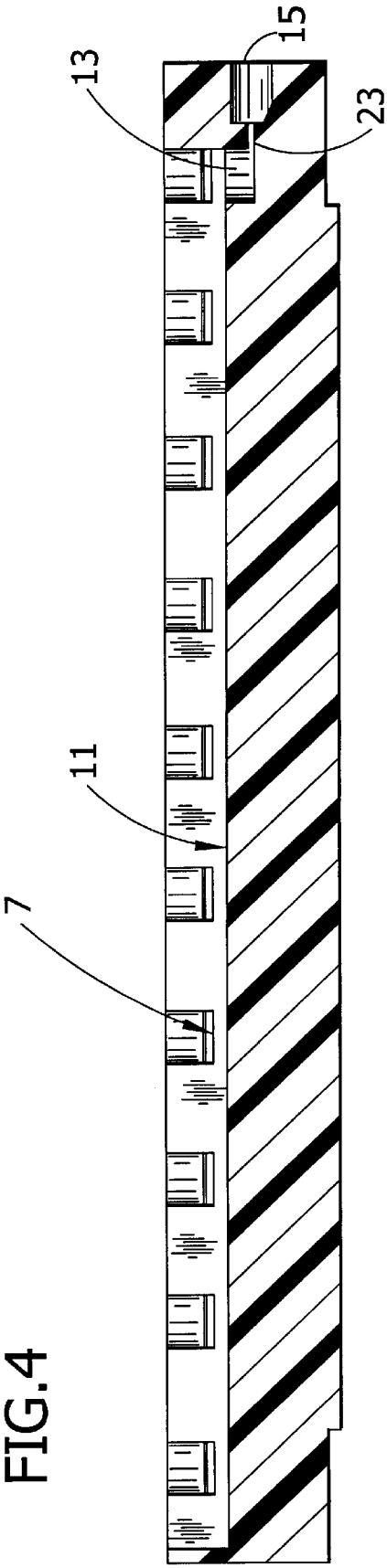
FIG. 4 is a sectional view taken along the plane of line 4—4 of FIG. 2.

Referring now to FIGS. 2–4, the collector 1 comprises a generally rectangular block 25 constructed from a material which, after thorough cleaning, will not leach metallic impurities into the solution. For example, the block 25 of the illustrated embodiment is constructed from Teflon.

The block 25 has a central waste trough 11 extending longitudinally within the upper surface of the block and multiple overflow spillways 7 extending laterally within the upper surface of the block in communication with the central waste trough. The waste trough 11 and spillways 7 are designated generally by their reference numbers. The receptacle troughs 7 each have a floor 27, an outer end 29 disposed generally adjacent a lateral edge margin of the upper surface of the block and an inner end 31 opening into the central waste trough 11. The floor 27 of each receptacle trough 7 slopes downward from the outer end 29 to the inner end 31 of the receptacle trough for delivering liquid in the receptacle trough to the central waste trough 11 (FIG. 3).

Vertically oriented receptacles 3 are formed in the block at the laterally outer end 29 of each spillway 7. The receptacles 3 open at their upper ends into the spillways 7 to allow overflow liquid from the receptacles to drain to the central waste trough 11. The diameter of each receptacle is sized to permit a sample collector 41 of the automated analytical instrumentation 4 (FIG. 1) to be dipped down into the receptacle 3 for collecting a sample to be analyzed. Each receptacle 3 also has an inlet 17 generally adjacent the bottom of the receptacle for receiving fluid into the receptacle (FIG. 3). The inlet 17 communicates with a respective inlet port 9 in a side wall of the block. The diameter of the inlet 17 is substantially reduced at an inner portion adjacent the receptacle for controlling the flow rate of liquid into the receptacle. The inlet port 9 communicates with the cleaning bath 8 (FIG. 1) by the bleed line 12 for receiving the liquid into the collector 1 to analyze the liquid.

With particular reference to FIG. 4, the central waste trough 11 slopes downward from a rear end of the block 25 toward a front end of the block to direct liquid in the waste trough 11 to a waste drain 13. The waste drain 13 has an outlet 23 generally adjacent the bottom of the waste drain for discharging liquid from the waste drain. The outlet 23 extends to an outlet port 15 in the front end of the block 25 for discharging liquid from the collector 1 to a suitable drainage system (not shown) or sewer (not shown) of the type well known to those of ordinary skill in the art.

The automated analytical instrumentation 4 (FIG. 1) is preferably a conventional instrumentation capable of detecting trace amounts of impurities in a liquid sample (e.g., Hewlett Packard 4500 ICP/MS machine). Such instrumentation includes atomic absorption, inductively-coupled plasma mass spectrometry (ICP/MS), capillary electrophoresis, and ion chromatography instrumentation.

The sample collection device 40 (FIG. 1) is preferably an autosampler designed for ICP/MS instrumentation (e.g., Cetac 500, commercially available from Cetac of Omaha; Gilson 222, commercially available from Gilson of England). Typically, these devices comprise a syringe or other suitable sampling device 41 which is inserted into the receptacle 3 through its opening 5 by a robotic arm or similar automated mechanism. Again through automation, the syringe extracts a sample of the cleaning solution from the receptacle 3. The syringe is then withdrawn from the receptacle and the contents of the syringe are analyzed.

In a preferred embodiment, the collector 1 comprises more than one receptacle so that a plurality of cleaning baths can be connected to the collector at the same time. As shown in FIG. 2, the collector 1 has two sets of ten receptacles 3, one set being on each side of the central waste trough 11. The receptacles 3 of each set are arranged in series, which in the illustrated embodiment is a line of equally spaced receptacles, to permit the instrumentation 4 to progressively dip into the receptacles one after another in a predetermined order. However, it is understood that the arrangement and number of receptacles 3 in the collector 1 may vary without departing from the scope of this invention. Each receptacle 3 would be connected to its own bleed line (not shown) to receive liquid from a different cleaning bath (not shown).

In operation, the recirculation pump 10 draws cleaning bath solution from the cleaning bath 8 and pumps the solution through the recirculation line 6. The recirculation pump 10 creates sufficient pressure in the recirculation line 6 such that a small portion of the cleaning solution is continuously diverted from the recirculation line, through the feed line 12 for delivery to the collector 1. The solution then flows through the inlet port 9 of the block 25 into the inlet 17. The inlet 17 meters the solution into the receptacle 3. Since the solution diverted through the inlet 17 is typically not returned to the cleaning bath 8, the diameter of the inlet is preferably minimized to prevent excessive depletion of the cleaning solution from the bath. For example, the inlet 17 of the illustrated embodiment is less than about ¼" in diameter, and more preferably about ⅛" in diameter.

The receptacle inlet 17 delivers liquid to the receptacle 3 at the bottom of the receptacle so that the liquid flows upward from the bottom of the receptacle. Filling the receptacle 3 from the bottom prevents stagnation of the solution in the receptacle 3. Further, by eliminating stagnation of the cleaning solution, the solution within the receptacle 3 at all times remains representative of the cleaning solution contained within the cleaning bath 8. Moreover, any contaminants which might be introduced from the syringe 41 of the sample collector device 40 do not enter the cleaning bath 8.

A continuing flow of solution into the receptacle 3 causes the solution to overflow to the receptacle into the spillway 7. The sloped floor 27 of the spillway 7 directs the overflow solution downward, away from the receptacle 3 and into the waste trough 11. The waste trough 11 receives the overflow liquid and directs the waste solution to the waste drain 13. The overflow solution exits the waste drain through the outlet 23, and is ultimately discharged from the block 25 to a suitable drainage system or sewer via the outlet port 15. No valves are used to shut off the flow of solution from the cleaning bath 8, thereby eliminating a source of contamination.

The syringe 41 or other sampling means of the automated analytical instrumentation is selectively inserted into the upper end of one of the receptacles 3 by a robotic arm 40 or the like. The syringe 41 automatically extracts a sample of the cleaning solution from the receptacle 3 and is withdrawn from the receptacle. The contents of the syringe 41 are then deposited in the ICP-MS machine of the automated analytical instrumentation 4.

In view of the foregoing, it will be seen that the several objects of the invention are achieved. The present invention is instrumental in obtaining more accurate and reliable sampling results by reducing the potential for contamination of the sample to be analyzed, such as through direct human contact or through the use of sampling devices or containers which are contaminated. Further, by providing a collector having receptacles adapted for directing overflow solution into respective spillways that run off into a waste trough for exhaustion from the collector, a representative sample of the cleaning bath can be maintained in the collector. In this way, an accurate reading of the level of contaminants in the cleaning solution entering the cleaning bath at a given moment can be obtained. The continuous feed system also reduces the complexity and risk of mechanical failure of the collector. The present invention also eliminates the need for valves or other similar devices, thereby reducing the risk of additional contamination of the sample being tested.

This collector also helps reduce the time required to sample and analyze a cleaning bath solution, as compared to existing "off-line" methods wherein the sample is collected and transported to a remote location for conducting the analysis. By utilizing the collector of the present invention, analytical instrumentation can be incorporated as an integral part of an "on-line" bath analysis system.

As various changes could be made in the above-described collector without departing from the scope of the invention, it is intended that all matter contained in the above description be interpreted as illustrative and not in a limiting sense.

What is claimed is:

1. A sample collection and analysis system for use in monitoring content of a liquid from at least one source of liquid, the system comprising:

a bleed line adapted for continuously open fluid communication with the liquid source;

a collector in continuously open fluid communication with the bleed line, the collector comprising at least one receptacle to receive liquid from said at least one source of liquid by way of the bleed line and to hold a quantity of the liquid for obtaining a sample, the receptacle having an inlet for receiving liquid into the receptacle from the bleed line and an open top;

the bleed line and collector being free of structure capable of stopping the flow of liquid from said at least one liquid source to the at least one receptacle whereby the liquid flows continuously into the at least one receptacle upon connection of the system to said at least one source of fluid;

a sample collecting device for collecting a sample of the liquid from the open top of the at least one receptacle, the receptacle being sized to permit reception of the sample collecting device therein; and a liquid analysis device for receiving liquid from tie sample collecting device and automatically analyzing the liquid for its content.

2. A sample analysis and collector system as set forth in claim 1 wherein the collector further comprises a port for connection to said at least one source of liquid, the port being constructed for permanent open fluid communication with the receptacle, the collector being incapable of blocking fluid communication from said at least one source of liquid through the port to the receptacle.

3. A sample analysis and collector system as set forth in claim 2 wherein the collector further comprises an inlet connecting the port and the receptacle, the inlet being sized to control the rate of flow of liquid from said at least one source of liquid into the receptacle.

4. A sample analysis and collector system as set forth in claim 1 having a plurality of receptacles and spillways for sampling liquid from a plurality of sources of liquid, each spillway being associated with a respective receptacle.

5. A collector as set forth in claim 4 having a waste trough in fluid communication with the spillways for carrying away overflow liquid flowing down the spillways.

6. A collector as set forth in claim 1 wherein the receptacles are arranged in a row and spaced at intervals selected to facilitate the operation of the sample collection device.

7. A collector as set forth in claim 1 wherein the source of liquid is a semiconductor wafer cleaning bath and the liquid is a cleaning bath solution.

8. A sample analysis and collector system as set forth in claim 1 wherein the bleed line and collector are free of flow control devices capable of stopping the flow of liquid from said at least one liquid source to the at least one receptacle.

9. A sample analysis and collector system as set forth in claim 8 wherein the bleed line and collector are free of valves capable of stopping the flow of liquid from said at least one liquid source to the at least one receptacle.

* * * * *